(12) United States Patent
Steinbacher et al.

(10) Patent No.: US 7,011,632 B2
(45) Date of Patent: Mar. 14, 2006

(54) METHODS AND APPARATUS FOR ULTRASONIC COMPOUND IMAGING

(75) Inventors: Franz Steinbacher, Vocklamarkt (AT); Josef Steininger, Vocklamarkt (AT)

(73) Assignee: Kretztechnik AG, Zipf (AT)

( * ) Notice: Subject to any disclaimer, the term of this patent is extended or adjusted under 35 U.S.C. 154(b) by 0 days.

(21) Appl. No.: 09/954,808

(22) Filed: Sep. 18, 2001

(65) Prior Publication Data

US 2003/0055334 A1 Mar. 20, 2003

(51) Int. Cl.
*A61B 8/00* (2006.01)

(52) U.S. Cl. .................. 600/437; 600/447; 600/463

(58) Field of Classification Search ......... 600/437–472
See application file for complete search history.

(56) References Cited

U.S. PATENT DOCUMENTS

| | | | |
|---|---|---|---|
| 5,568,813 A | | 10/1996 | Deitrich et al. |
| 5,623,928 A | * | 4/1997 | Wright et al. ............... 600/447 |
| 5,793,701 A | * | 8/1998 | Wright et al. .................. 367/7 |
| 5,873,830 A | * | 2/1999 | Hossack et al. ............ 600/447 |
| 5,891,038 A | * | 4/1999 | Seyed-Bolorforosh et al. ......................... 600/447 |
| 5,980,459 A | * | 11/1999 | Chiao et al. ................ 600/447 |
| 6,048,315 A | * | 4/2000 | Chiao et al. ................ 600/447 |
| 6,050,942 A | * | 4/2000 | Rust et al. .................. 600/443 |
| 6,056,693 A | * | 5/2000 | Haider ........................ 600/443 |
| 6,117,081 A | * | 9/2000 | Jago et al. .................. 600/443 |
| 6,117,082 A | * | 9/2000 | Bradley et al. ............. 600/447 |
| 6,193,659 B1 | * | 2/2001 | Ramamurthy et al. ...... 600/443 |
| 6,193,663 B1 | * | 2/2001 | Napolitano et al. ......... 600/447 |
| 6,213,947 B1 | * | 4/2001 | Phillips ....................... 600/443 |
| 6,221,018 B1 | * | 4/2001 | Ramamurthy et al. ...... 600/443 |
| 6,277,073 B1 | * | 8/2001 | Bolorforosh et al. ....... 600/437 |
| 6,315,723 B1 | * | 11/2001 | Robinson et al. ........... 600/443 |
| 6,436,046 B1 | * | 8/2002 | Napolitano et al. ......... 600/447 |
| 6,530,885 B1 | * | 3/2003 | Entrekin et al. ............ 600/437 |

* cited by examiner

*Primary Examiner*—Brian L. Casler
*Assistant Examiner*—William C. Jung
(74) *Attorney, Agent, or Firm*—McAndrews, Held & Malloy, Ltd.; Peter J. Vogel; Michael A. Dellapenna

(57) ABSTRACT

Methods and apparatus for achieving a compound ultrasound imaging mode are disclosed. The methods include a step of firing a plurality of ultrasound beams at a single location, receiving first and second echoes, and combining the first and second echoes to form a composite scan line. The following beam parameters may be varied: transmission focus depth, transmission aperture, transmission frequency, and transmission burst length. Echoes may vary in one or both of receive bandwidth and receive center frequency. In one embodiment, transmission focus depth, transmission aperture, and receive center frequency all differ between the beams. A weighting step may be performed before or after the summing step. The apparatus may include vector memory, a compound logic processor for weighting and summing the vectors, and memory for storing the summed vectors.

21 Claims, 2 Drawing Sheets

METHODS AND APPARATUS FOR ULTRASONIC COMPOUND IMAGING

BACKGROUND OF THE INVENTION

The present invention is generally directed to apparatus and methods for ultrasound imaging. More particularly, the present invention is directed to apparatus and methods for achieving a compound mode.

In conventional ultrasound imaging systems, there is an array of ultrasonic transducers. The ultrasonic transducers are used to transmit an ultrasound beam and then receive the echoes from an object being studied. An array for ultrasound imaging typically has a plurality of transducers positioned in a line and driven with separate voltages. By selecting the time delay or phase and amplitude of the applied voltages, the individual transducers can be controlled to produce ultrasonic waves. The ultrasonic waves combine to form a net ultrasonic wave that travels along a preferred vector direction and is focused at a selected point along the beam.

Multiple firings may be used to obtain data that represents the same anatomical information. The beamforming parameters of each of the firings may be varied to provide a change in maximum focus or otherwise change the content of the received data for each firing. For example, the multiple firings may comprise successive beams transmitted along the same scan line with the focal point of each beam being shifted relative to the focal point of the previous beam. By changing the time delay and amplitude of the applied voltages, the beam with its focal point can be moved in a plane to scan the object.

Reception of reflected sound by a transducer involves the same principles as transmitting sound. The voltages produced at the receiving transducers are summed so that the net signal is representative of ultrasound echoes reflected from a single focal point in the object. As with the transmission mode, this focused reception of the ultrasonic energy is achieved by separate time delays (and/or phase shifts) and gains provided to the signal by each receiving transducer.

Imaging with conventional ultrasound systems can result in images containing a significant amount of speckle. Speckle is an imaging artifact produced from interference patterns of multiple receive echoes. Speckle appears as mottling which is manifest as black holes in the image.

A method has been proposed to reduce speckle by combining vector data from multiple ultrasound firings for different portions of a scan line. The input vector data from multiple firings is combined to take advantage of the best range(s) of data from each receive firing. One or more lines are fired at the same location, with the lines having different focus points or depths. Compounding of echoes from the multiple firings (focused to different depths) is performed over only a fraction of the length of the scan line. Compounding portions of scan lines from echoes of different transmissions does not entirely remove speckle. A need exists for more effective methods and apparatus for reducing the amount of speckle in ultrasound images.

A conventional compounding technique is the compounding of frames rather than lines. The technique of compounding of frames has a disadvantage of movement artifact.

Conventional multifocus algorithms create zones where the near field and far field come together and may create image impressions if an operator were to move from the near field to the far field in a small range. Thus, there is a need for an ultrasound mode that reduces the border between the near field and the far field.

Some conventional ultrasound techniques do not have much penetration. Examination of some patients, particularly patients having high adipose content tissue, may require ultrasound capable of deeper penetration. Accordingly, there is a need for ultrasound devices or techniques that provide greater penetration.

BRIEF SUMMARY OF THE INVENTION

In accordance with at least one embodiment, a method is provided which comprises a step of transmitting two or more ultrasound beams at the same scan position. The beams may differ in at least one of the following parameters: transmission focal depth, transmission aperture, transmission frequency, and transmission burst length. Echoes from the beams may differ in one or both of received bandwidth and receive center frequency. In one embodiment, the transmit beams differ in transmission focal depth and transmission aperture, and the echoes vary in receive center frequency.

One embodiment of the present invention comprises the steps of transmitting first and second ultrasound beams along a common scan line into a region of interest (ROI) of a patient and receiving first and second echoes from the ROI, the first echo representing reflections along an entire scan line of the first ultrasound beam, the second echo representing reflections of the entire scan line of the second ultrasound beam. A further step is combining the first and second echoes along the entire scan line to form a composite scan line in an ultrasound image.

Methods in accordance with the present invention may comprise multiplying the first and second echoes with at least one weighting factor to form first and second weighted echoes, and summing the first and second weighted echoes. The weighting factor may equal 1/N, wherein N is equal to a number of ultrasound beams transmitted along a common scan line in the transmitting step.

In still a further embodiment of the present invention, the transmitting step further comprises transmitting the first and second ultrasound beams at different focus depths and at different transmission apertures, and the receiving step further comprises receiving the first and second echoes at different receive center frequencies. Further, the first and second echoes are scaled by a factor of 1/N.

BRIEF DESCRIPTION OF THE DRAWINGS

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION OF THE INVENTION

Figure 1:
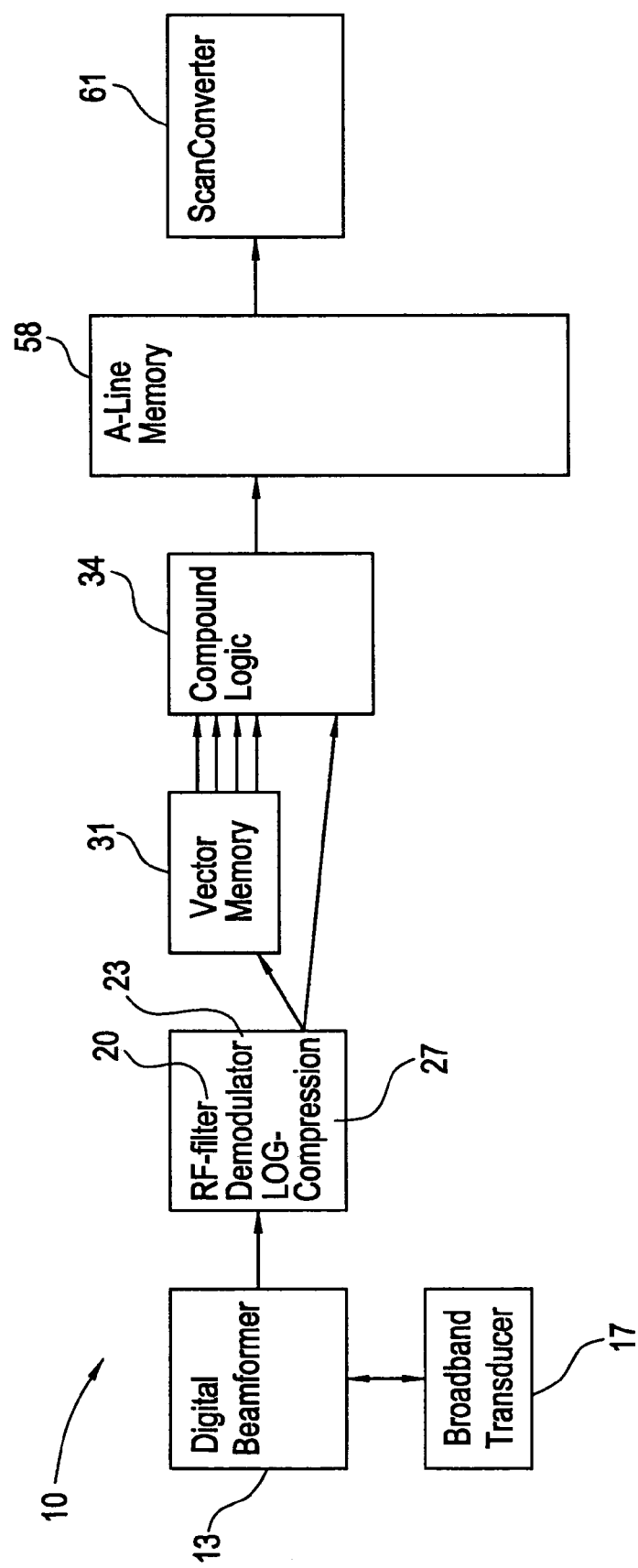
FIG. 1 is a block diagram of an apparatus in accordance with the present invention.

FIG. 1 is a block diagram of a device 10 in accordance with one embodiment of the present invention. The device 10 comprises a digital beamformer 13 that controls a broadband transducer 17 and receives signals from the broadband transducer 17. The digital beamformer 13 may be any beamformer suitable for forming B-images. A suitable broadband transducer 17 operates at a range of frequencies such as 2 MHz to 4 MHz, for example, however other frequency ranges are suitable. The lower frequency achieves depth and the higher frequency is transmitted for the near field.

In accordance with an aspect of some embodiments of the present invention, two or more ultrasound beams are transmitted at the same scan position. The beams may differ in any one or more of the following parameters: transmission focus depth, transmission aperture, transmission frequency, and transmission burst length. Echoes from the transmitted beams may vary in one or both of receive bandwidth and receive center frequency. In one embodiment, transmission focus depth, transmission aperture, and receive center frequency all differ between the beams.

After being received, the echo data pass through a bandpass filter 20, a demodulator 23, and a LOG compressor 27. The pass band frequency range of the bandpass filter 20 depends on the receive center frequency. The receive center frequency depends on the bandwidth of the broadband transducer 17. After bandpass filtering, demodulation, and LOG compression, a data set representative of a series of echoes received along an entire single beam (hereafter "beam data") is stored in vector memory 31. The data sets stored in the vector memory 31 are stored in the form of vector data sets, wherein each vector data set corresponds to the full length of a beam or scan line in a field of view.

In one embodiment, after the last beam of the plurality of beams has been fired at a single location, the data from the last beam are transmitted to a compound logic processor 34 and the data from the previous beams that had been stored in vector memory are also transmitted to the compound logic processor 34. For example, if the total number of beams fired at a single location is two, then the first beam is stored in vector memory 31 after being fired. After the second beam is fired, the data from the first beam are transmitted by the vector memory 31 to the compound logic processor 34, and the data from the second beam are transmitted to the compound logic processor 34. If, for example, the total number of beams fired at a single location is four, then the first three beams are stored in vector memory 31 after being fired. After the fourth beam is fired, the data from the first three beams are transmitted by the vector memory 31 to the compound logic processor 34, and the data from the fourth beam are transmitted to the compound logic processor 34.

At least two beams may be fired at a single location. In one embodiment, five beams are fired at a single location. As a greater number of beams are fired at a single location, the frame rate may slow down.

Various transducer arrays may be employed in accordance with embodiments of the present invention. For example, the transducer array 17 may be 1D or 2D.

Beam focusing may be accomplished by various methods. For example, different delay times may be provided, the delay times varying from outer transducer elements to a central transducer element.

The transmitting step may include transmitting first and second ultrasound beams at different first and second transmission focus depths. In one embodiment, the first transmit beam may be near field and the second transmit beam may be far field, providing greater penetration and increasing the homogeneity between the near field and the far field. The focus depth on the near field may be provided by controlling the delay times on apertures during transmission. For example, the second beam may be provided with a different delay time than the first beam. The first beam may also have a different transmit frequency than the second beam. In an alternative embodiment, the second transmit beam may be near field and the first transmit beam may be far field.

Each aperture may transmit from all elements of the aperture at a common center frequency and in a common direction. Alternatively, steering of the transmit beam may be performed. Steering may be accomplished, for example, by providing the elements in a single aperture with different delays.

In some embodiments, the first and second ultrasound beams may be transmitted at different first and second transmission apertures. For example, if the focus depths between the first and second transmissions are very different, different apertures may be needed for the two transmissions. Generally, larger apertures are needed for the far field, and smaller apertures are needed in the near field.

Various techniques can be used to control the transducer array to simultaneously receive echoes along multiple scan lines. In some embodiments of the present invention, the transducer array is controlled to receive echoes simultaneously along multiple scan lines in order to keep the frame rate up despite multiple firings at one line.

Figure 2:
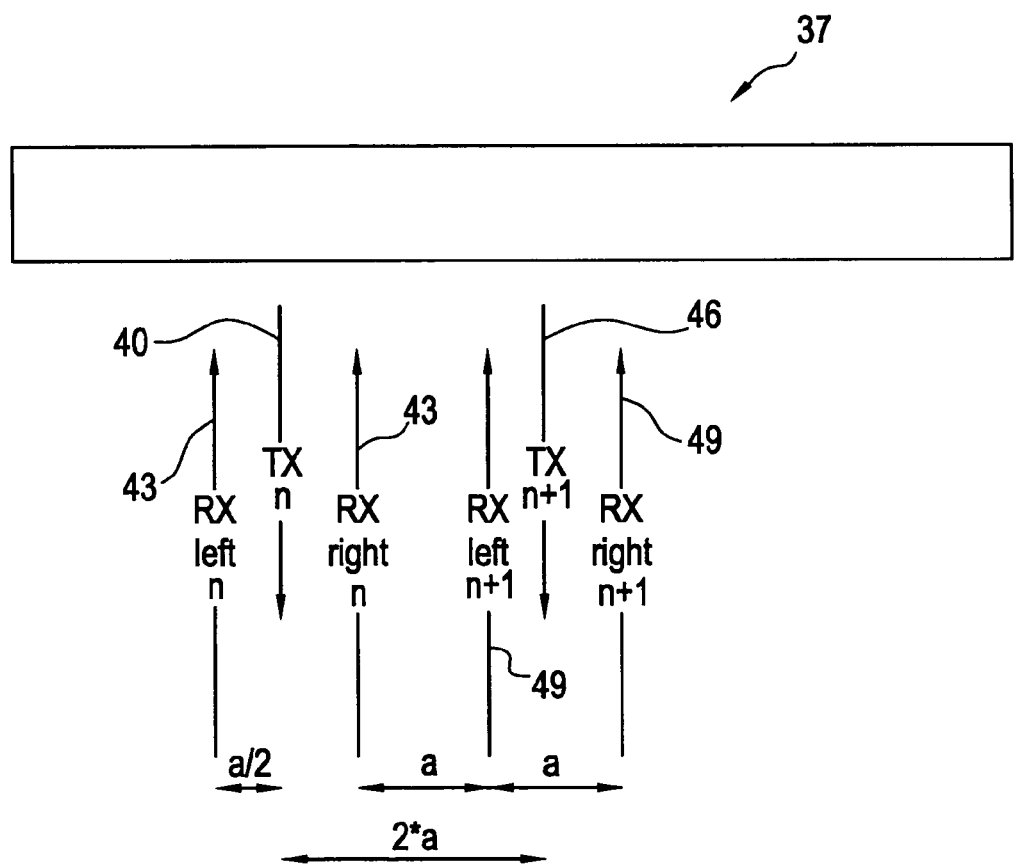
FIG. 2 is a schematic diagram of a method for receiving multibeams.

As seen in FIG. 2, there is a probe 37 having transducer elements (not shown). For a transmission (TX) firing 40, at least two receive (RX) echoes 43 are received simultaneously. The two RX echoes 43 are separated symmetrically left and right relative to the TX beam 40. The two RX 43 echoes are from the same transmission firing, TX beam 40.

The distance between the displayed receive echoes is (a), and the distance between the TX beam 40 and adjacent RX echoes 43 is a/2. The distance to the next TX beam, which is designated TX (n+1) 46, from the TX beam 40 is 2*a. Two RX echoes 43 are received by the same elements on the probe 37. Also, two RX (n+1) echoes 49 are received by the same elements on the probe 37. The distance (a) between the receive echoes RX 43 must be small compared to the width of a receiving aperture in order for the two echoes RX 43 to be received at positions symmetrically left and right relative to the TX beam 40. Similarly, the distance (a) between the receive echoes RX (n+1) 49 must be small compared to the width of a receiving aperture 52 in order for the two echoes RX (n+1) 49 to be received at positions symmetrically left and right relative to the TX (n+1) beam 46.

Returning to FIG. 1, when the beam data (vector data sets) are in the compound logic processor 34, the beam data are summed. Compound logic is a step of combining the vector data sets to form an entire composite scan line. In some embodiments, the compound logic processor 34 performs a weighting (or scaling) step either before or after summing. The scaling step forms first and second weighted echoes in embodiments in which first and second echoes comprise the beam data and when scaling is performed prior to summing. The scaling factor may equal 1/N, where N stands for the number of ultrasound beams fired per location. N may be any integer of two or greater. In one embodiment, N=5, which provides a sufficient frame rate and still provides desirable penetration depth and speckle suppression. The adder that is in the compound logic processor 34 performs the summing step. The summing step and scaling step may be represented by (I1*k+I2*k+ . . . IN*k) where IN is the Nth vector and k is the weighting or scaling factor. The summing step and scaling step may also be represented by k*(I1+I2+ . . . IN). The scaling factor k equals 1/N in some embodiments.

Following processing in the compound logic processor 34, the result of the combined vectors (or scaled and summed vectors in some embodiments) is stored in A-line memory 58. One line of memory in the A-line memory 58 thus has the compound logic result of the two or more vectors that correspond to all of the multiple lines fired at a single position.

Summing of the vectors that correspond to the multiple lines fired at a single position occurs over the entire length of the vectors. Summing over the entire length can have a filtering effect on speckle, thereby suppressing speckle.

By combining line-by-line rather than frame-by-frame, some embodiments in accordance with the present invention produce images that are homogeneous or smooth from near field to the far field. Being smooth from the near field to the far field can be advantageous in applications where a border between the near field and the far field would interfere with imaging.

In embodiments that vary frequency and focus between first and second transmission beams, more penetration is possible in different applications. It may be desirable, for example, to have deeper penetration in patients with a large amount of adipose tissue.

After the execution of all of the scan positions, A-line memory 58 will have stored a complete frame or B-image. The data from the A-line memory 58 is converted by a digital scan converter 61 in a fashion similar to standard B-image processing. After scan conversion, the data may be further processed, displayed, or stored in any suitable manner. For example, the data may be printed, displayed on a monitor, or stored in B-cine memory.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for obtaining ultrasound images, comprising:
   transmitting first and second ultrasound beams along a common scan line into a region of interest (ROI) of a patient;
   receiving a plurality of first and second echoes from said ROI, said plurality of first echoes representing reflections along an entire scan line of said first ultrasound beam, said plurality of second echoes representing reflections of said entire scan line of said second ultrasound beam;
   multiplying said plurality of first echoes and said plurality of second echoes with at least one weighting factor to form a first plurality of weighted echoes and a second plurality of weighted echoes; and
   summing said plurality of first and second of weighted echoes along said entire scan line.

2. The method of claim 1, wherein said transmitting step further comprises: transmitting said first and second ultrasound beams at different first and second transmission frequencies.

3. The method of claim 1, wherein said transmitting step further comprises: transmitting said first and second ultrasound beams at different first and second transmission burst lengths.

4. The method of claim 1, wherein said transmitting step further comprises: transmitting said first and second ultrasound beams at different first and second transmission focus depths.

5. The method of claim 1, wherein said transmitting step further comprises: transmitting said first and second ultrasound beams at different first and second transmission apertures.

6. The method of claim 1, wherein said receiving step further comprises: receiving said plurality of first and second echoes at different first and second receive frequencies.

7. The method of claim 1, wherein said receiving step further comprises: receiving said plurality of first and second echoes at different first and second receive bandwidths.

8. The method of claim 1, wherein said receiving step further comprises: receiving said plurality of first and second echoes at different first and second receive focus depths.

9. The method of claim 1, wherein the at least one weighting factor equals 1/N, wherein N is equal to a number of ultrasound beams transmitted along a common scan line in said transmitting step.

10. The method of claim 9, wherein:
    said transmitting step further comprises transmitting said plurality of first and second ultrasound beams at different focus depths end at different transmission apertures; and
    said receiving step further comprises receiving said plurality of first and second echoes at different receive center frequencies.

11. The method of claim 1, wherein said transmitting step transmits at least three ultrasound beams and said receiving step receives at least three echoes along said entire scan line that are combined to form said composite scan line.

12. A method for obtaining ultrasound images, comprising:
    transmitting first and second ultrasound beams along a common scan line into a region of interest (ROI) of a patient;
    receiving a plurality of first and second echoes from said ROI, said plurality of first echoes representing reflections along an entire scan line of said first ultrasound beam, said plurality of second echoes representing reflections of said entire scan line of said second ultrasound beam; and
    combining said plurality of first and second echoes along said entire scan line to form a composite scan line in an ultrasound image, wherein said combining comprises: (a) multiplying said plurality of first echoes and said plurality of second echoes with at least one weighting factor to form a first plurality of weighted echoes and a second plurality of weighted echoes; and (b) summing said plurality of first and second weighted echoes along said entire scan line,
    wherein said first and second ultrasound beams are focused at predetermined different first and second depths along said entire scan line.

13. A method for obtaining ultrasound images, comprising:
    transmitting first and second ultrasound beams along a common scan line into a region of interest (ROI) of a patient;
    receiving a plurality of first and second echoes from said ROI, said plurality of first echoes representing reflections along an entire scan line of said first ultrasound beam, said plurality of second echoes representing reflections of said entire scan line of said second ultrasound beam; and multiplying said plurality of first echoes and said plurality of second echoes with at least one weighting factor to form a first plurality of weighted echoes and a second plurality of weighted echoes; and summing said plurality of first and second weighted echoes along said entire scan line, wherein said first and second ultrasound beams are generated by exciting a plurality of transducer elements defining an aperture size of a probe, said first and second ultrasound beams being generated with a different number of transducer elements corresponding to different first and second aperture sizes.

14. The method of claim 13, wherein said receiving step further comprises: receiving said plurality of first and second echoes at different first and second receive focus depths.

15. A method for obtaining ultrasound images, comprising:

transmitting first and second ultrasound beams along a common scan line into a region of interest (ROI) of a patient, said first and second ultrasound beams being transmitted at different focus depths and at different transmission apertures;

receiving first and second echoes from said ROI, said first echo representing reflections along an entire scan line of said first ultrasound beam, said second echo representing reflections of said entire scan line of said second ultrasound beam, said first and second echoes being at different receive center frequencies;

multiplying said first and second echoes by a weighting factor equal to 1/N to form first and second weighted echoes, wherein N is equal to a number of ultrasound beams transmitted along a common scan line in said transmitting step; and summing said first and second weighted echoes along said entire scan line to form a composite scan line in an ultrasound image.

16. A method for obtaining ultrasound images, comprising:

transmitting first and second ultrasound beams along a common scan line into a region of interest (ROI) of a patient;

receiving a plurality of first echoes and a plurality of second echoes from said ROI, said plurality of first echoes being received simultaneously and representing reflections along an entire scan line of said first ultrasound beam, said plurality of second echoes being received simultaneously and representing reflections along said entire scan line of said second ultrasound beam;

multiplying said plurality of first echoes and said plurality of second echoes with at least one weighting factor to form a first plurality of weighted echoes and a second plurality of weighted echoes;

summing said first and second pluralities of weighted echoes along said entire scan line; and combining said first plurality of weighted echoes and second plurality of weighted echoes along said entire scan line to form a composite scan line in an ultrasound image.

17. The method of claim 16, wherein said receiving step further comprises: receiving said first plurality of echoes and said second plurality of echoes at different first and second receive frequencies.

18. The method of claim 16, wherein said receiving step further comprises: receiving said first plurality of echoes and said second plurality of echoes at different first and second receive bandwidths.

19. The method of claim 16, wherein the at least one weighting factor equals 1/N, wherein N is equal to a number of ultrasound beams transmitted along a common scan line in said transmitting step.

20. The method of claim 19, wherein:

said transmitting step further comprises transmitting said first and second ultrasound beams at different focus depths and at different transmission apertures; and said receiving step further comprises receiving said first plurality of echoes and said second plurality of echoes at different receive center frequencies.

21. The method of claim 16, wherein said receiving step further comprises: receiving said plurality of first echoes and said plurality of second echoes at different first and second receive focus depths.

* * * * *